(12) United States Patent
Shimazu et al.

(10) Patent No.: US 7,836,755 B2
(45) Date of Patent: Nov. 23, 2010

(54) SOLIDIFICATION SENSOR

(75) Inventors: Hiromi Shimazu, Kashiwa (JP);
Hiroyuki Ohta, Tsuchiura (JP); Yohei Tanno, Hitachinaka (JP); Mari Uchida, Tsuchiura (JP); Naoto Saito, Kasumigaura (JP)

(73) Assignee: Hitachi, Ltd., Tokyo (JP)

( * ) Notice: Subject to any disclaimer, the term of this patent is extended or adjusted under 35 U.S.C. 154(b) by 133 days.

(21) Appl. No.: 11/943,753

(22) Filed: Nov. 21, 2007

(65) Prior Publication Data

US 2008/0121024 A1    May 29, 2008

(30) Foreign Application Priority Data

Nov. 24, 2006 (JP) ................ 2006-316443

(51) Int. Cl.
G01N 33/00 (2006.01)
G01N 37/00 (2006.01)
G01N 33/18 (2006.01)
G01N 33/487 (2006.01)

(52) U.S. Cl. ................ 73/61.41; 73/61.44

(58) Field of Classification Search ..... 73/61.41–61.44, 73/61.71
See application file for complete search history.

(56) References Cited

U.S. PATENT DOCUMENTS

| | | | |
|---|---|---|---|
| 3,102,420 A * | 9/1963 | Mason | .......... 73/765 |
| 6,201,980 B1 * | 3/2001 | Darrow et al. | .......... 600/347 |
| 6,370,964 B1 * | 4/2002 | Chang et al. | .......... 73/862.046 |
| 6,854,317 B2 * | 2/2005 | Porter et al. | .......... 73/31.05 |
| 7,168,294 B2 * | 1/2007 | Porter et al. | .......... 73/31.05 |
| 7,395,693 B2 * | 7/2008 | Porter et al. | .......... 73/23.2 |
| 2006/0043508 A1 * | 3/2006 | Ohta et al. | .......... 257/417 |
| 2007/0295061 A1 * | 12/2007 | Gerlach et al. | .......... 73/61.41 |

FOREIGN PATENT DOCUMENTS

| | | |
|---|---|---|
| JP | 03007817 A * | 1/1991 |
| JP | 2004-003889 | 1/2004 |

OTHER PUBLICATIONS

Q. T. Trinh, G. Gerlach, J. sorber, K.-F. Arndt. "Hydrogel-based piezoresistive pH sensors: Design, simulation and output characteristics." Sensors and Actuators B 117. Available online Dec. 13, 2005. <www.sciencedirect.com>.*

K. Rajanna, M. M. Nayak. "Strain Sensors." J. Webster (ed.), Wiley Encyclopedia of Electrical and Electronics Engineering. 1999. pp. 566-580.*

(Continued)

*Primary Examiner*—Lisa M Caputo
*Assistant Examiner*—Punam Roy
(74) *Attorney, Agent, or Firm*—Antonelli, Terry, Stout & Kraus, LLP.

(57) ABSTRACT

In a solidification sensor for measuring a solidification state of a liquid with a high degree of accuracy in real time, and for making the sensor small-sized with a reduced power consumption, the solidification sensor comprises a liquid absorbing portion formed of a liquid absorbable material, a substrate coupled to the liquid absorbing portion and a strain sensor for measuring strain exerted to the substrate due to a volumetric change upon solidification of a liquid absorbed in the liquid absorbing portion.

14 Claims, 5 Drawing Sheets

OTHER PUBLICATIONS

Felt. (2005). In the Crystal Reference Encyclopedia. West Chiltington, West Sussex: Crystal Reference. Retrieved Aug. 26, 2009, from http://www.credoreference.com/entry/cre/felt.*

Fabric. (1993). In the Webster's Third New International Dictionary, Unabridged. Retrieved Aug. 26, 2009, from http://lionreference.chadwyck.com/.*

D. N. Bittner and E. D. Adams. "Solidification of Helium in Confined Geometries." Journal of Low Temperature Physics. vol. 97, Nos. 5/6. (1994) pp. 519-535.*

K. H. Ip, P. K. Dutta, D. Hui. "Effects of low temperature on the dynamic moduli of thick composite beams with absorbed moisture." Composites: Part B. 32 (2001) pp. 599-607.*

* cited by examiner

SOLIDIFICATION SENSOR

FIELD OF THE INVENTION

The present invention relates to a sensor for detecting a solidification state of a liquid.

DESCRIPTION OF RELATED ART

As a technology for measuring a solidification state of a liquid, for example, JP-A-2004-3889 discloses such a measurement that an expansion of a container containing a liquid, caused by a phase transition of the liquid, is detected in view of a variation in a light beam passing an optical fiber provided in the container.

However, the above-mentioned technology indispensably utilizes a light source and a measuring instrument, and as a result, there has been caused such a problem that the measuring apparatus becomes large-sized. Should a wireless system be used for detecting a solidification state, the sensor must be driven by a battery, but in the case of the disclosed sensor, a power consumption of the sensor would be too large to drive it by a battery.

Further, there has been a method of indirectly detecting a solidification state by detecting a temperature at which occurrence of a solidification is expected. However, this method causes such a problem that an accurate measurement is difficult in the case of a supercooling phenomenon or in such a case that a melting point varies by impurities contained in a liquid to be measured.

SUMMARY OF THE INVENTION

Thus, an object of the present invention is to provide a small-sized solidification sensor with a low power consumption, which can measure a solidification state of a liquid on a real time base.

To the end according to the present invention, there is provided a solidification sensor comprising a liquid absorbing portion formed of a member which can absorb thereinto a liquid, a substrate coupled to the liquid absorbing portion, and a strain sensor for measuring a strain in the substrate, wherein a strain is caused in the substrate due to a volumetric change of a liquid absorbed in the liquid absorbing portion upon solidification of the liquid, and the strain is detected by means of the strain sensor so as to detect the solidification of the liquid.

In the present invention, a volumetric change occurs when the liquid absorbed in the liquid absorbing portion is changed from a liquid phase to a solid phase. Since this volumetric change causes the liquid absorbing portion to vary its length, and as a result, a strain is exerted to the substrate coupled to the liquid absorbing portion, the variation in the strain can be detected with a high degree of accuracy, and thus it is possible to detect a solidification state of the liquid which corresponds to the variation in the strain.

Other objects, features and advantages of the invention will become apparent from the following description of the embodiments of the invention taken in conjunction with the accompanying drawings.

BRIEF DESCRIPTION OF SEVERAL VIEWS OF DRAWING

Figure 12:
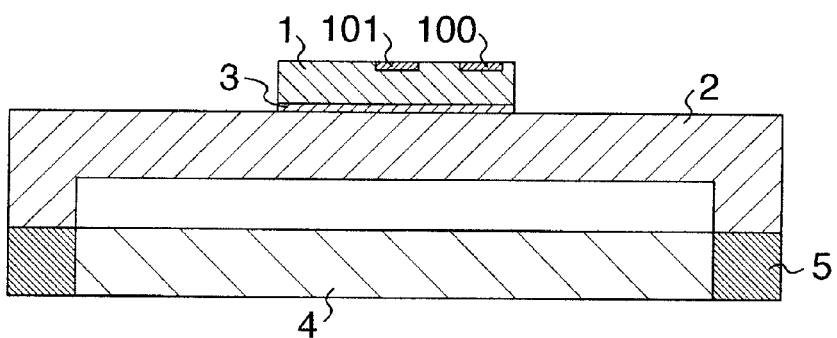
Figure 13A:
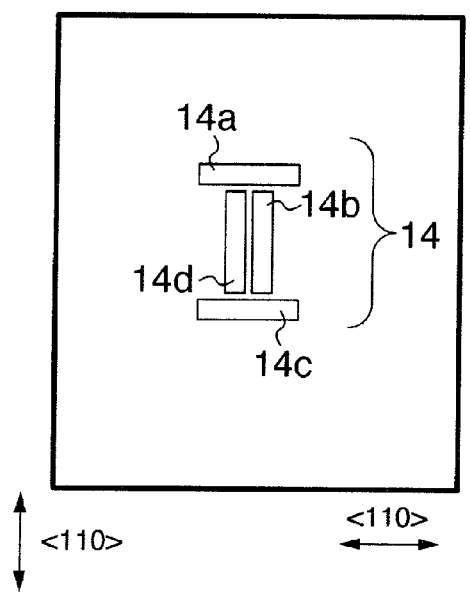
Figure 13B:
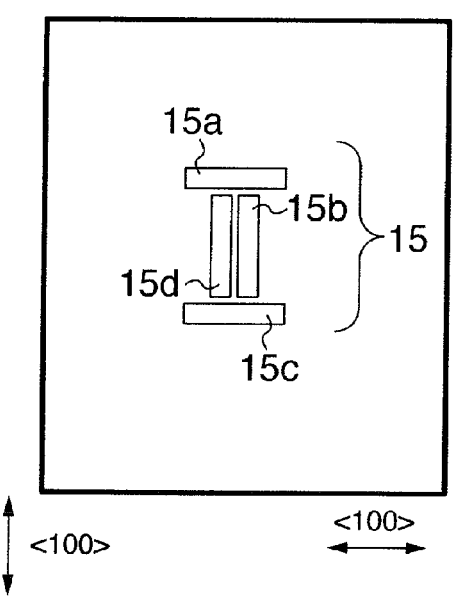

FIG. 12 is a sectional view illustrating a structure of a modification of the solidification sensor according to the first embodiment of the present invention, FIG. 13A is a view illustrating an arrangement of a strain sensor used in the first embodiment of the present invention, and FIG. 13B is a view illustrating an arrangement of a strain sensor used in the first embodiment of the present invention.

DETAILED DESCRIPTION OF THE INVENTION

Explanation will be made of preferred embodiments according to the present invention with reference to the accompanying drawings.

Embodiment 1

At first a first embodiment according to the present invention will be explained with reference to FIG. 1, which is a sectional view illustrating a main part of a solidification sensor according to the present invention.

Figure 1:
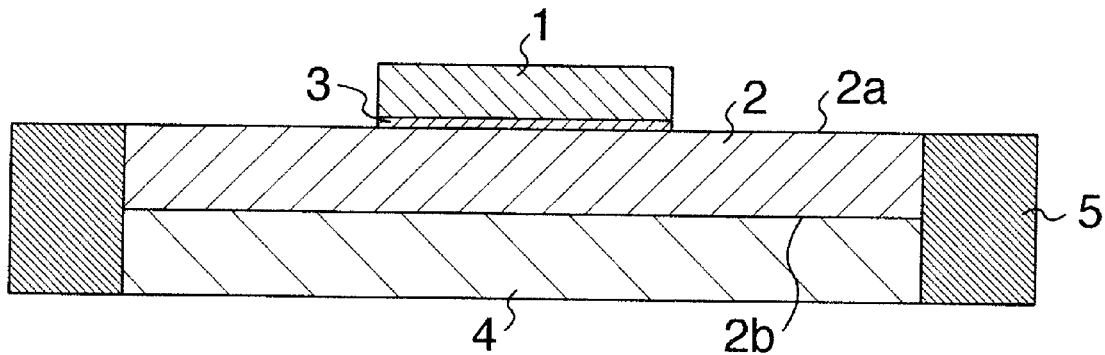
FIG. 1 is a sectional view illustrating a structure of a main part of a solidification sensor according to a first embodiment of the present invention.

In the solidification sensor in the embodiment shown in FIG. 1, at least a strain sensor 1 is provided on one side surface 2a of a substrate 2 through the intermediary of an adhesive layer 3, and a liquid absorbing portion 4 is provided on the other side surface 2b of the substrate 2, being coupled to the substrate 2 through the intermediary of a connecting portion 5. Then, the solidification sensor is arranged in such a way that the liquid absorbing portion 4 is soaked in a liquid of which a solidification state is to be detected.

With this embodiment, in the liquid absorbed in the liquid absorbing portion 4, a volumetric change is caused when a phase transition from its liquid phase to a solid phase occurs as the temperature of the liquid becomes lower. If the liquid is a latent heat storage, the liquid causes a volumetric contraction so that the length of the liquid absorbing portion 4 varies in response to a volumetric change thereof, and accordingly, a strain is exerted to the substrate 2 coupled to the liquid absorbing portion 4. Accordingly, a variation in the strain can be detected by the strain sensor 1 with a high degree of accuracy.

Figure 6:
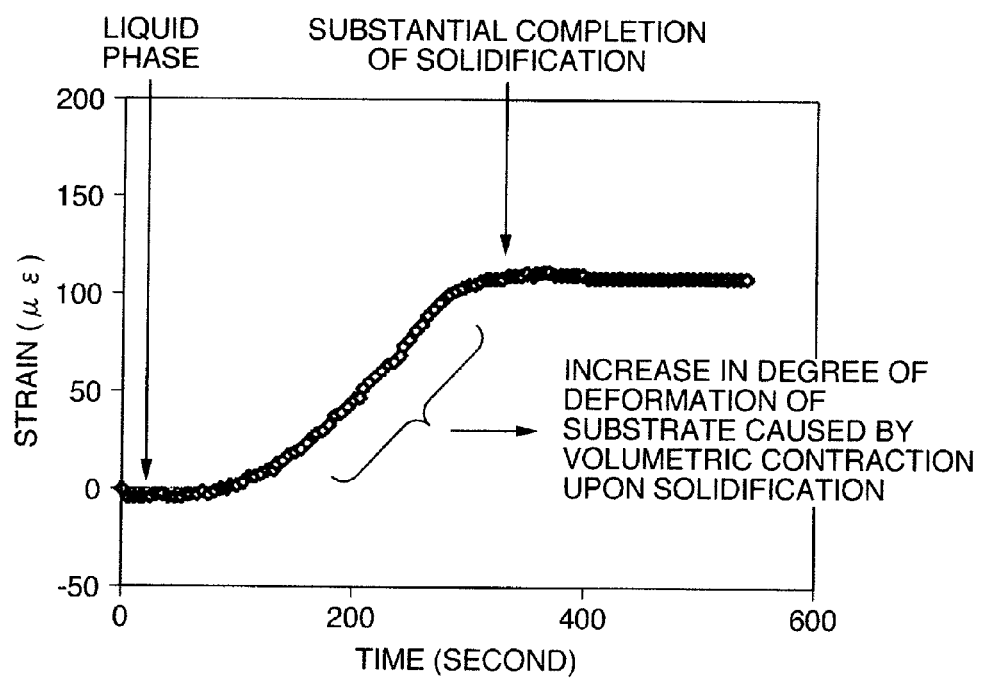
FIG. 6 is a graph illustrating an example of data measured by the solidification sensor according to the first embodiment of the present invention.

As the liquid is cooled and cooled, the liquid absorbing portion 4 contracts in response to a solidification of the liquid, and accordingly, the substrate 2 is deformed into a U-like shape. The deformation of the substrate becomes larger as the solidification rate increases. FIG. 6 shows results of measurements by the solidification sensor in this embodiment. A strain exerted to the substrate was measured when the object to be measured was changed from its liquid phase to a solid phase as time passed, and as a result, it has been found that the strain was increased as soon as the solidification thereof was initiated, and after completion of the solidification, the strain become constant. With the relationship between the solidification state and the degree of strain, a solidification state of the liquid can be measured in real time.

Further, by detecting a decrease in the strain of the substrate 2 when the temperature is raised, a phase transition through which the solidified liquid is melted and returned from a solid phase to a liquid phase can be detected.

It is noted that the solidification sensor according to the present invention can be used for measurement of even a liquid to be measured, such as a water, which increases in volume upon solidification. In this case, in a liquid state, should no strain be exerted on the substrate 2 as shown in FIG. 1, it would be expected such a risk that the liquid absorbing portion 4 is bent outward when the liquid absorbing portion 4 is expanded upon solidification, and accordingly, no strain is exerted to the substrate 2. Thus, the shapes of the substrate 2 and the liquid absorbing portion 4 have to be adjusted in such a condition that the volume of the liquid absorbing portion 4 is large. For example, the length of the liquid absorbing portion 4 may be less so that a strain is exerted to the substrate 2 in the liquid phase while the strain of the substrate 2 is decreased when the liquid absorbing portion 4 expands upon solidification of the liquid.

It is noted that the strain sensor 1 preferably has a strain detecting part formed from an impurity layer formed in a semiconductor substrate. The direction of measurement by the strain sensor is adjusted to the longitudinal direction of the substrate 2. With the strain detecting part formed from the impurity layer, the power consumption can be reduced, and a strain exerted to the substrate 2 can be detected with high sensitivity.

Further, with a configuration of the strain detecting part of the strain sensor 1 forming a Wheatstone bridge circuit which is composed of four impurity layers, a variation in resistance value caused by a temperature can be restrained, and accordingly, measurements of a strain with a high degree of accuracy or measurements of a solidification state can be possible.

Moreover, in the case of the semiconductor substrate made of a silicon monocrystal, impurity diffusion resistances constituting the Wheatstone bridge circuit may be composed of four p-type diffusion layers 14a to 14d whose longitudinal directions are set in the direction of <110> of silicon monocrystal on a silicon substrate having a (100) surface, as shown in FIG. 13A, or composed of four n-type diffusion layers 15a to 15d whose longitudinal directions are arranged in the direction of <100> of silicon monocrystal, as shown in FIG. 13B, thereby it is possible to enhance the sensitivity and the effect of restraining variation in output caused by a temperature variation.

<Coupling Between Substrate and Liquid Absorbing Portion>

It is noted that FIG. 1 shows such a configuration that the substrate 2 and the liquid absorbing portion 4 are coupled to each other at both ends thereof through the intermediary of connecting portions 5.

Thus, in the case of fixing them at both ends, as shown in the drawing, it is advantageous as the deformation of the substrate becomes larger. However, even with no fixing at both ends, there may be also used such a configuration that a strain is effected at a place where the strain sensor is attached on the substrate 2, when the liquid absorbing portion 4 causes a volumetric change.

Figure 2:
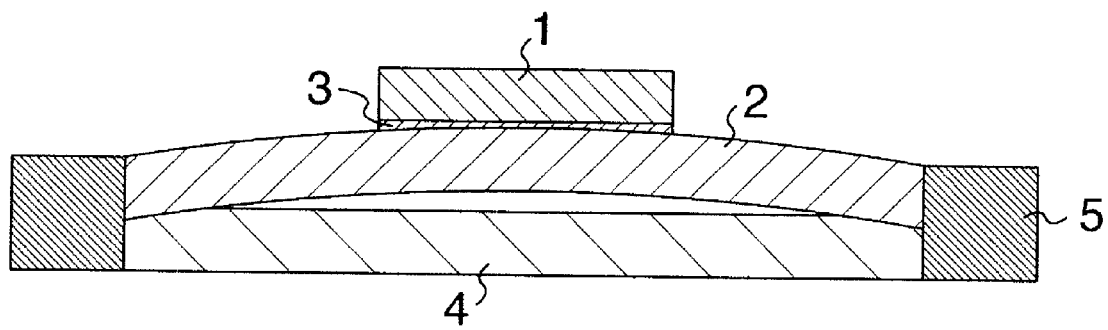
FIG. 2 is a sectional view illustrating a structure of a main part of a modification of the solidification sensor according to the first embodiment of the present invention.

Although FIG. 1 shows such a configuration that the substrate 2 and the liquid absorbing portion 4 have the same length, the liquid absorbing portion 4 may be shorter than the substrate 2 so that the substrate 2 is formed into an U-like shape, as shown in FIG. 2. This configuration offers such an advantage that a deformation of the substrate 2 can be conveniently led in a single direction (resulting in bending deformation). Further, there would be offered such an advantage that the liquid absolving portion can be prevented from becoming slackness.

Figure 3:
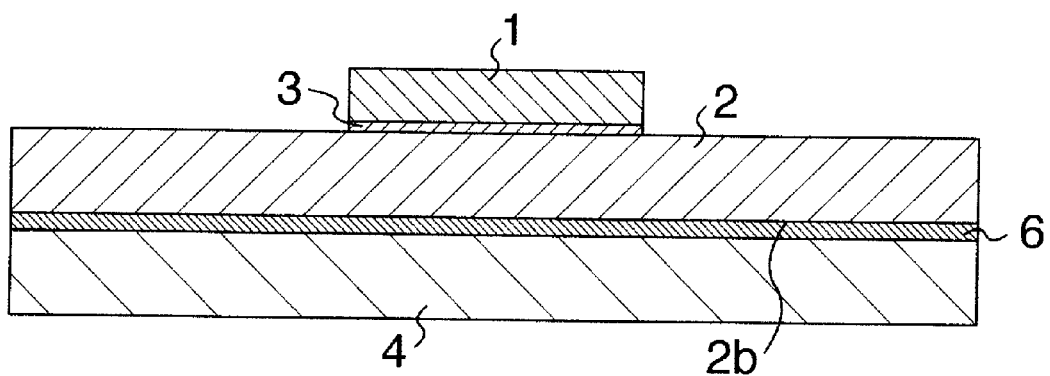
FIG. 3 is a sectional view illustrating a structure of a main part of a modification of the solidification sensor according to the first embodiment of the present invention.

Further, as shown in FIG. 3, upon coupling between the substrate 2 and the liquid absorbing potion 4, if the substrate 2 is coupled with the liquid absorbing portion 4 by means of a connecting layer 6 over its one side surface 2b in its entirety, there may be offered such an advantage that the liquid absorbing portion can conveniently transmits a volumetric change to the substrate 2.

The connecting portions 5 are made by an adhesive, a tape, fastening of bolts, caulking or the like. In the case of the fastening of bolts or the caulking, the coupling between the substrate 2 and the liquid absorbing portion 4 can be firmly made. In this case, with the provision of a metal plate outside of the substrate 2 and the liquid absorbing portion 4, the coupling may be firmer.

Further, with the provision of the substrate 2 which is rectangular in a top plan view, the strain field of the substrate 2 may be a uniaxial strain field in the direction of long sides of a rectangle, and by setting the measuring direction of the strain sensor in the long side direction of the rectangle, the relationship between a strain measured by the strain sensor 1, and a solidification state may be relatively simplified.

Figure 4:
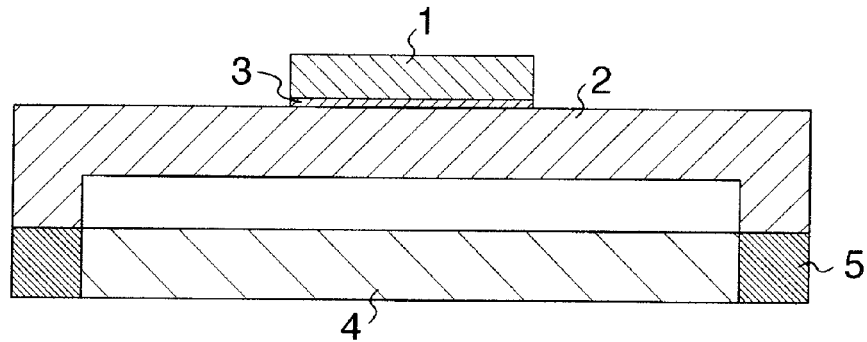
FIG. 4 is a sectional view illustrating a structure of a main part of a modification of the solidification sensor according to the first embodiment of the present invention.

Further, as shown in FIG. 4, with such a structure that the substrate 2 provided with the strain sensor is bent around its end portions toward the liquid absorbing portion 4, that is, with the substrate 2 having a U-like cross-sectional shape, the liquid absorbing portion 4 can be prevented from being exerted thereto with a mechanical load in such a case that a liquid absorbed in the liquid absorbing portion 4 is in a liquid phase. Moreover, a deformation can be conveniently transmitted to the substrate 2 when the liquid is solidified. Further, there may be exhibited such an advantage that the strain sensor 1 can be kept away from a liquid surface.

Figure 5:
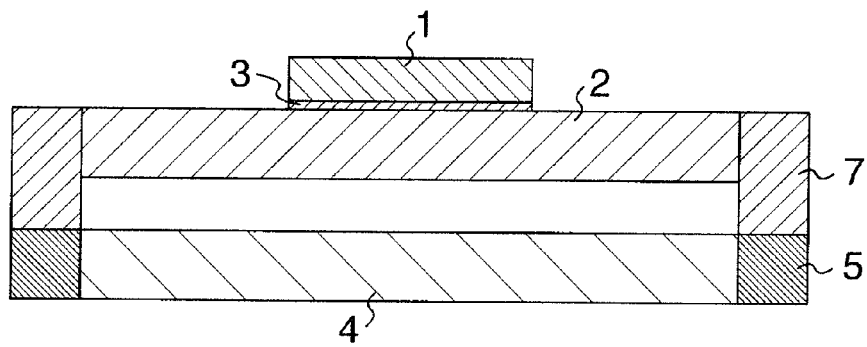
FIG. 5 is a sectional view illustrating a structure of a main part of a modification of the solidification sensor according to the first embodiment of the present invention.

Further, as an example variant from the U-like shape substrate 2 shown in FIG. 4, the substrate 2 may be provided at its both ends with different members in a U-like shape as shown in FIG. 5. Even with this configuration, advantages similar to that exhibited by the configuration shown in FIG. 4 can be obtained.

Further, as the material of the substrate 2, there may be preferably used a material such as metal, which cannot absorb a liquid, and accordingly, the deformation of the substrate 2 is only caused by a deformation of the liquid absorbing portion 4, thereby it is possible to measure a solidification state with a high degree of accuracy.

The substrate 2 may also be made of resin or the like. However, in this case, the substrate 2 is preferably coated with a material which can hardly absorb therein a liquid over its entire surface in order to measure a solidification state with a high degree of accuracy.

Further, the liquid absorbing portion 4 is made of a material, for example, a cloth such as nonwoven fabric, or sponge which can easily absorb a liquid and be easily deformed, and accordingly, it can soon cause a volumetric change, thereby it is possible to increase deformation (strain) to be transmitted to the substrate 2.

Figure 11:
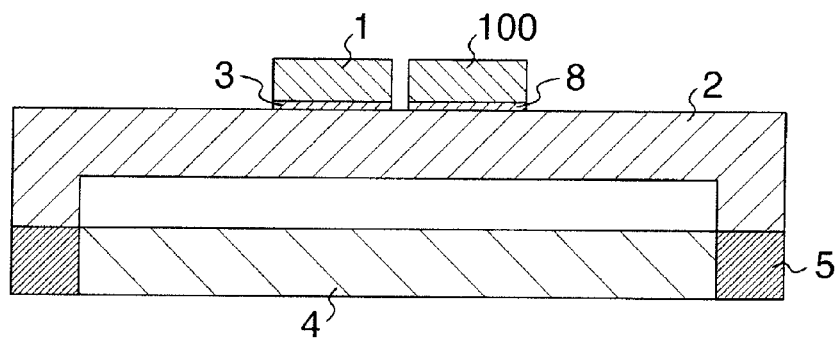
FIG. 11 is a sectional view illustrating a structure of a modification of the solidification sensor according to the first embodiment of the present invention.

Further, as shown in FIG. 11, with the provision of the strain sensor 1 and a temperature sensor 100 mounted on the substrate 2, a variation in the output of the strain sensor caused by a temperature can be corrected. At this stage, the temperature sensor 100 is preferably arranged in the vicinity of the strain sensor 1.

Further, as shown in FIG. 12, a strain detecting portion 101 and the temperature sensor 100 may be formed within the strain sensor 1. With this configuration, a variation in an output of the strain sensor caused by a variation in temperature can be corrected with a high degree of accuracy, and further, there may be offered such a merit that the structure of the apparatus can be simplified. It is noted that the temperature sensor 100 may be formed of a PN junction type diode. With this configuration, the temperature sensor can be simply provided on the strain sensor, and according, it is possible to prevent the temperature sensor from being affected by a variation in strain, thereby it is possible to precisely measure a variation in temperature around the strain detecting portion. In the case of forming the strain detecting portion 101 and the temperature sensor 100 in the strain sensor 1, it is desirable to provide the strain detecting portion 101 in the center part of the strain sensor 1 but to provide the temperature sensor 100 in a part which is nearer to the periphery of the substrate, than the strain detecting portion 101. With this configuration, a strain exerted to the substrate can be measured with a higher degree of accuracy, and further, correction can be made for variation in output caused by a temperature, thereby it is possible to measure a solidification state with a high degree of accuracy.

Embodiment 2

Next, an explanation will be made of a second embodiment according to the present invention with reference to FIG. 7, which shows a main part of a mechanical quantity measuring device in the second embodiment, and like reference numerals are used to denote like parts to those explained in the first embodiment.

Figure 7:
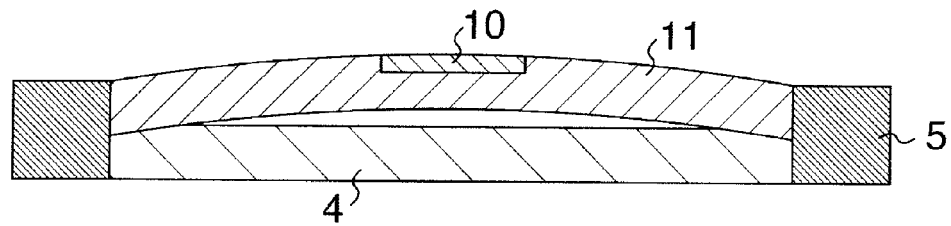
FIG. 7 is a sectional view illustrating a structure of a main part of a solidification sensor according to a second embodiment of the present invention.
Figure 8:
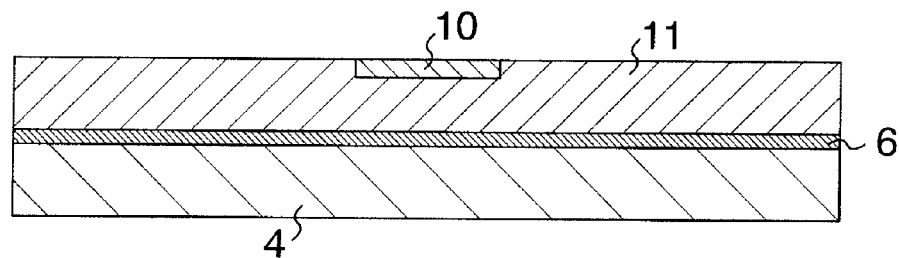
FIG. 8 is a sectional view illustrating a structure of a modification of the solidification sensor according to the second embodiment of the present invention.

Although the strain sensor 1 is attached to the substrate 2 through the intermediary of an adhesive 3 in the solidification sensor explained in the first embodiment and shown in FIGS. 1 to 5, the mechanical quantity measuring device in this embodiment shown in FIG. 7 has such a configuration that a strain detecting portion 10 is provided on the outer surface of a silicon substrate 11 which is coupled to the liquid absorbing portion 4 by means of the connecting portions 5. It is noted that the strain detecting portion 10 is formed of, for example, an impurity diffusion resistance which is formed by introducing impurities such as arsenic, phosphorous or boron, in the outer surface of the silicon substrate.

With this configuration, the same technical effects and advantages as those obtained in the first embodiment can be obtained. Further, in this embodiment, since the strain detecting portion 10 is provided, directly on the outer surface of the silicon substrate 11, no provision of an adhesive layer is required between the strain sensor and the substrate on which the strain sensor is provided, and accordingly, a strain to the substrate can be directly detected, thereby it is possible to carry out measurements with a high degree of accuracy. Further, since no risk of deterioration of the adhesive layer is caused, there can be exhibited such an advantage that a highly reliable solidification sensor can be offered.

It is noted that although the explanation has been made of using the silicon substrate in this embodiment, not only a silicon substrate but also any other semiconductor substrate may be used with the same technical effects and advantages.

The solidification sensor according to the present invention is provided in a constant temperature transportion container for regenerative medical treatment and a solidification state of latent heat storage charged in the container is measured in real time so as to make it possible to optimize an amount of the medium to be charged in the container, and accordingly, to obtain a highly reliable constant temperature transportion container for regenerative medical treatment. Further, with the provision of the solidification sensor according to the present invention and a heating unit in the transportion container, the heating unit is turned on and off in response to a result of measurement by the solidification sensor, thereby it is possible to maintain the temperature in the transportion container at a desired value.

Although explanation has been hereinabove made of such an example that the solidification sensor is used for the latent heat storage, it is noted that the present invention should not be limited to this example. That is, the present invention can be applied for any other material which can be changed from a liquid phase to a solid phase and which can cause a volumetric change that may be caused by either expansion or contraction. It has been confirmed that the solidification sensor according to the present invention can detect a solidification state as to a latent heat storage such as water through experiments.

Figure 9:
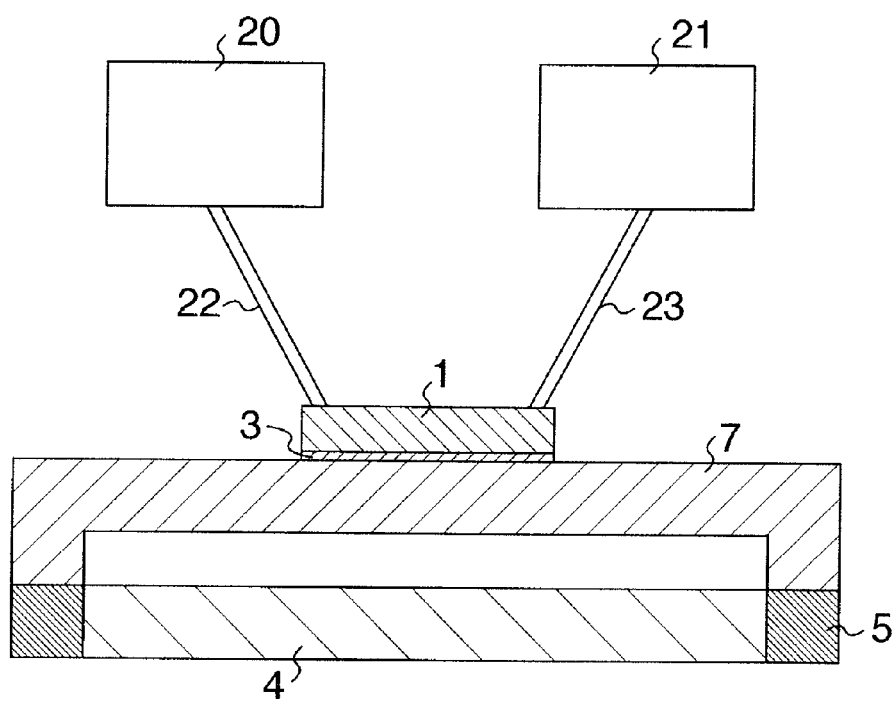
FIG. 9 is a view for explaining a measuring method with one use of the solidification sensor according to the present invention.

Further, in the case of detecting a solidification state with the use of the solidification sensor according to the present invention, as shown in FIG. 9, the strain sensor 1 in the solidification sensor is connected thereto with a power source through the intermediary of a wiring 22, and is also connected to a volt meter 21 through the intermediary of a wiring 23 in order to measure a solidification state. That is, it is noted that a variation in voltage corresponds to a variation in strain, that is, a solidification state.

Figure 10:
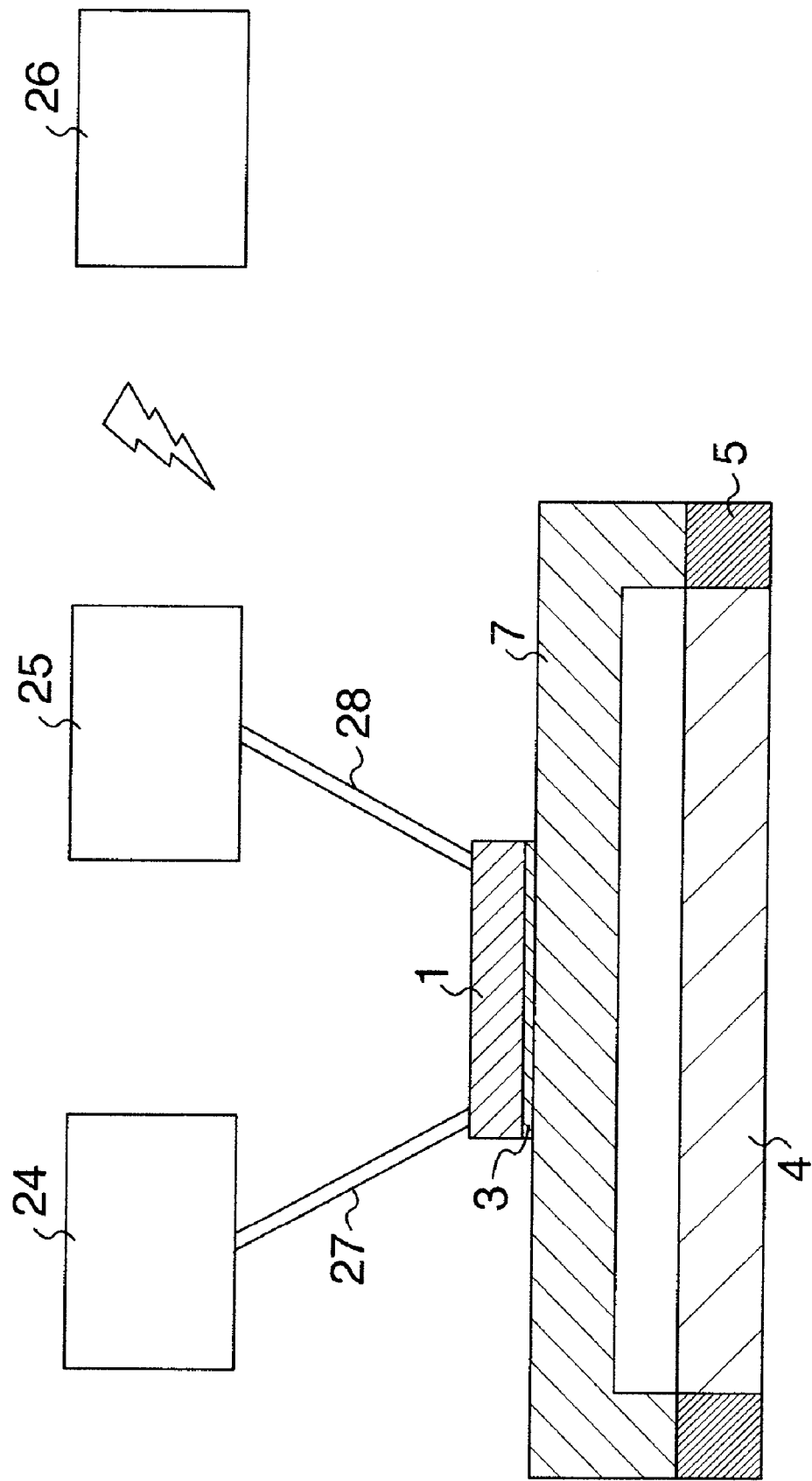
FIG. 10 is a view for explaining another measuring method with another use of the solidification sensor according to the present invention.

Further, as shown in FIG. 10, the strain sensor 1 in the solidification sensor according to the present invention may be connected to a battery 24 through the intermediary of a wiring 27, and may be also connected to a transmitter module 25 through the intermediary of a wiring 28, thereby it is possible to receive data measured by the solidification sensor, by means of a receiver module 26 in a wireless manner.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A solidification sensor comprising:
 a substrate having first and second opposite surfaces and two ends;
 a strain sensor provided on the first surface of the substrate;
 a liquid absorbing portion provided on the second surface of the substrate, and formed of a member configured to absorb a solidifiable liquid;

connecting portions that couple the substrate and the liquid absorbing portion at both of the two ends of the substrate;

wherein the strain sensor measures a strain exerted to the substrate due to a volumetric change of the liquid absorbed in the liquid absorbing portion upon solidification of the liquid, so as to detect the solidification of the liquid; and wherein the strain sensor has a bridge which is formed of an impurity layer on a silicon substrate.

2. A solidification sensor as set forth in claim 1, wherein the substrate provided with said strain sensor is rectangular.

3. A solidification sensor as set forth in claim 2, wherein the member of the liquid absorbing portion is formed of a deformable material that absorbs the liquid.

4. A solidification sensor as set forth in claim 3, wherein the member of the liquid absorbing portion is one of a strip-shaped non-woven fabric and a strip-shaped sponge.

5. A solidification sensor as set forth in claim 1, wherein the substrate provided with the strain sensor has a cross-sectional shape in the form of the letter U.

6. A solidification sensor as set forth in claim 1, wherein a length of the liquid absorbing portion is shorter than that of the substrate provided with the strain sensor.

7. A solidification sensor as set forth in claim 1, wherein the substrate is made of metal material.

8. A solidification sensor as set forth in claim 1, wherein said strain sensor has four p-type impurity layers which are arranged in a direction of <110>.

9. A solidification sensor as set forth in claim 1, wherein said strain sensor has four n-type impurity layers arranged in a direction of <100>.

10. A solidification sensor as set forth in claim 1, further comprising a temperature sensor.

11. A solidification sensor as set forth in claim 10, wherein said temperature sensor is provided in the strain sensor.

12. A solidification sensor as set forth in claim 1, wherein said strain sensor is one of directly and indirectly disposed on the first surface of said substrate.

13. A solidification sensor as set forth in claim 12, wherein said strain sensor is indirectly disposed on the first surface of said substrate via an adhesive layer.

14. A solidification sensor as set forth in claim 1, wherein the liquid solidifies from a liquid phase to a solid phase in response to a change in temperature.

* * * * *